(12) United States Patent
Reinkensmeyer et al.

(10) Patent No.: US 6,613,000 B1
(45) Date of Patent: Sep. 2, 2003

(54) METHOD AND APPARATUS FOR MASS-DELIVERED MOVEMENT REHABILITATION

(75) Inventors: David J. Reinkensmeyer, Irvine, CA (US); Christopher C. Painter, Irvine, CA (US); Clifton T. Pang, San Jose, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/967,641

(22) Filed: Sep. 28, 2001

Related U.S. Application Data
(60) Provisional application No. 60/237,065, filed on Sep. 30, 2000.

(51) Int. Cl.[7] .......................... A61B 5/103; A61B 5/117
(52) U.S. Cl. ..................................................... 600/587
(58) Field of Search ........................... 600/587, 588, 600/300; 345/156, 167, 161, 701; 463/36; 434/236; 708/140; 341/20, 27

(56) References Cited

U.S. PATENT DOCUMENTS

| | | | | |
|---|---|---|---|---|
| 6,206,702 B1 | * | 3/2001 | Hayden et al. | 434/236 |
| 6,225,977 B1 | * | 5/2001 | Li | 345/156 |
| 6,261,239 B1 | * | 7/2001 | Abraham-Fuchs et al. | 600/558 |

* cited by examiner

*Primary Examiner*—Max F. Hindenburg
*Assistant Examiner*—Brian Szmal
(74) *Attorney, Agent, or Firm*—Daniel L. Dawes; Myers Dawes Andras & Sherman LLP (57) ABSTRACT

A computer-based system provides arm movement therapy for patients with sensory motor impairments. The system is based off a web site that provides access to assessment and therapy exercises designed to test and improve motor coordination in the arm. It operates over the World Wide Web using client-side applets, and can track user movement recovery over time and report it to a remote server computer. The system can also be customized to provide a personalized program of therapeutic exercise to a multiplicity of individuals. A mass manufactured computer input device senses the user's movement and provides a means to track sensory motor performance.

38 Claims, 8 Drawing Sheets

● = FORCES STARTED AT TWO SECONDS
× = FORCES STARTED AT ONE SECOND
MT = MOVEMENT TIME TO COMPLETE TRIAL WITH STANDARD DEVIATION
DIST = DISTANCE MOVED AFTER FORCE ACTIVATION WITH STANDARD DEVIATION
TP = TOTAL CUMULATIVE PRACTICE TIME WITH STANDARD DEVIATION

```
●    = FORCES STARTED AT TWO SECONDS
×    = FORCES STARTED AT ONE SECOND
MT   = MOVEMENT TIME TO COMPLETE TRIAL WITH STANDARD DEVIATION
DIST = DISTANCE MOVED AFTER FORCE ACTIVATION WITH STANDARD DEVIATION
TP   = TOTAL CUMULATIVE PRACTICE TIME WITH STANDARD DEVIATION
```

METHOD AND APPARATUS FOR MASS-DELIVERED MOVEMENT REHABILITATION

RELATED APPLICATIONS

The present application is related to and claims priority from U.S Provisional Patent Application 60/237,065, filed Sep. 30, 2000.

BACKGROUND OF THE INVENTION

1. Field of the Invention

The invention relates to the field of apparatus and methods using computer-controlled rehabilitation or physical therapy in combination with a computer network. More specifically, the invention relates to an Internet-based rehabilitation system for treatment of injury and disease.

2. Description of the Prior Art

Stroke is the largest single cause of major disability in our nation with approximately 730,000 Americans having a new or recurrent stroke every year. As a result of their stroke, people often lose strength, speed, and coordination in their hand and arm or other motor functions. Post-stroke rehabilitation therapy is an important process in the recovery of stroke patients who, with practice, can for example improve their ability to reach, grasp, and manipulate objects. Although rehabilitation immediately after the stroke has more significant effects, improvements even several years after a brain injury are still possible. With the assistance of a physical or occupational therapist, stroke patients are able to improve their sensory motor skills by repetitive movements. These movements help stimulate recovery of the nervous system and aid the patient in relearning how to use their limbs.

With the high cost of medical care in the country today, many patients lack the monetary means to continue hands on therapy with a professional therapist for long periods of time. As a result, the patients are forced to go home earlier following their stroke without getting the post stroke therapy necessary for continued recovery. Further, there is a lack of technology to allow the patients to do their own therapy at home.

There are several examples of prior art systems that describe computer controlled rehabilitation or physical therapy in combination with a computer network. In general, these systems describe methods by which a rehabilitation therapist can interact with a remote patient in real-time. For example, Burgess, described below, teaches a method for providing physical therapy to a remote human client that includes a communication link that provides real-time sound and video images of the patient to the therapist, and vice versa. Girone et.al. and Hogan et.al., described below, teach telerehabilitation systems that are formed by a pair of rehabilitation devices with a first device at the therapist and a second device coupled to the client's limbs. The therapist interacts in real-time with the patient by moving or feeling the movement of the first device, which moves or responds to the movement of the second device.

None of these prior art systems describe how a large number of patients could simultaneously access individualized therapy exercises remotely and autonomously from a therapist. This is significant because there is a very large number of survivors of stroke in the country who could benefit from ongoing rehabilitation exercise. Providing directly supervised therapy to this large population, even if it were done remotely, would be prohibitively costly. In addition, recent research has indicated that simple, highly repetitive exercise can improve sensory motor recovery. Such exercise can be performed without direct, moment-by-moment supervision of a therapist.

Recently, several robotic systems have been developed that physically interact with the patient to mimic the aid that would be provided by a real therapist and retrain coordinated movement (for example, see Hogan et al., below). Although preliminary trials show promise in the realms of improved evaluation and therapy, these robotic systems are not cost nor size efficient, making them impractical for common everyday home use.

Burgess, "Method and System for Providing Physical Therapy Services," U.S. Pat. No. 6,007,459 (1999) shows in FIG. 1, method 10 which includes the step 12 of providing an electronic communication link between a human client and a therapist that provides real-time video, sound, and data from the client to the therapist and vice versa. Step 14 of the method involves instructing the client to move in a particular manner or to assume a sustained posture. Further, the method includes step 16 involving the requesting of feedback from the client relating to bodily sensation corresponding to the movement or sustained posture. At step 20, the feedback is used to assess the physical condition of the client and at step 22, remedial movements or a remedial sustained posture is communicated to the client to address the physical condition.

As shown in FIG. 2, in response to a preliminary diagnosis, step 32 refers the client to an interactive terminal, which links the client and remotely located physical therapist through video images and sound. As shown in FIG. 3, system 40 includes a communication link 42, a first terminal 44 associated with a client and a second terminal 46 associated with a therapist.

As shown in FIG. 4, the system includes a goiniometer, an accelerometer, a dynamometer, reflex testing devices or other postural measurement devices coupled with the first terminal 4.

Burgess is described generally as being performed on "a communication link" in which the therapist is remote from the patient, but interacting in real-time with the to patient.

Schenck et.al., "Therapy Apparatus Having a Passive Motion Device for Flexing a Body Member," U.S. Pat. No. 5,746,704 (1998) describes an apparatus which is programmed or controlled to provide an upper range of motion or extension separated from a lower range of motion or flexion. When using device 10 to flex a finger 12, the device 10 can be supported to the patient's wrist by a variety of means. As shown in FIG. 1, the slide guide 16 can be integral with a cast or wrist brace 92. Accordingly, the wrist brace 92 will be formed from a lightweight plastic material. To affix the finger 12 to the carriage 14, a connector 94, such as a rubber band or the like can be attached to the finger 12 and wrapped around the carriage 14, such as in an annular groove 96 formed in the outer surface 26 of the cylindrical carriage 14 intermediate the ends thereof.

Miller, "Exercise Apparatus," U.S. Pat. No. 5,755,645 (1998) shows an exercise apparatus, which when in use requires a user grasping limb interface 8 shown in FIGS. 1–3 can move limb interface 8 in the directions indicated by arrows D1–3 in a spherical configuration anywhere within the three dimensional resistance field 90 to exercise a full functional motion. Computer 110 can be programmed to provide resistance field 90 with separate areas of varied resistance. With reference to FIG. 3, limb interface 8 includes an outer yoke 120 which is secured to the distal end of arm member 18. An intermediate yoke 122 is rotatably mounted to outer yoke 120 along an axis 121 by rotary joints 128a and 128b. An inner yoke 124 is rotatably mounted to intermediate yoke 122 along an axis 123 by rotary joint 130. This configuration provides limb interface 8 with a gimbal joint 7 having three unbraked rotational degrees of freedom. The gimbal joint 7 allows the user's hand to be comfortably oriented at almost any position relative to exercise apparatus 10 during use.

Girone et.al., "Ankle Rehabilitation Systems," U.S. Pat. No. 6,162,189 (2000) shows in FIGS. 3A and 3B detailed views of the connection of foot attachment 24 to mobile platform 25 in rehabilitation device 12. Force sensor 36 is positioned between foot attachment 24 and mobile platform 25. Force sensor 36 measures in real time forces applied from foot 11 to mobile platform 25'. As shown in FIG. 5, controller interface 14 receives position measurement data 49 and force measurement data 39 from rehabilitation device 12. Position and force output 57 from analog-to-digital converter 56 is received at personal computer board 58. Pressure sensors 61 interface piston 42 of rehabilitation device 12 to generate piston pressure measurement data 60 from each compartment of piston 42.

Host computer 18 determines desired force and position measurement data 65 for rehabilitation device 12. Desired force and position measurement data 65 is applied to interface software module 66. Interface software module 66 determines, from sensor output 64 and desired force and position measurement data 65, the pressure to be applied to each piston 42 for providing desired force feedback and position of rehabilitation device 12. In FIG. 16, a real-time telerehabilitation system can be formed of a pair of rehabilitation devices with a first device at a therapist location and a second device coupled to the user's foot. A therapist specialist 202 manipulates the local rehabilitation device 12b, which interfaces with the remote rehabilitation device 12a. Teleconferencing connection 210 connects host computer 18 and remote computer 23.

Lander et.al., "Tactile Feedback Controlled by Various Medium," U.S. Pat. No. 5,984,880 (1999) shows in FIG. 2, the system includes a first force-feedback assembly 1/15 comprising a force source 1 supplying the artificial hand 51 with a variable force value and a sensor 15 which monitors the hand movement. A digital word may be fed to the devices 51 and 52 by the computer 54 in some cases, thus producing an exact ratio or feedback between the force of device 51 and the force of device 52 depending upon the position constant of the force-feedback device 52 and the position constant of the artificial limb 51. Usually, the force of the force-feedback device 52 and the feedback of artificial limb 51 will be varied as a function of system forces, user interactive forces, virtual environment objects or a selected blend of these including computer 54 output.

Hogan et al., "Interactive Robot Therapist," U.S. Pat. No. 5,466,213 (1995) shows in FIGS. 5a and 5b, the robotic therapist 10 to which patient 12 is secured can be controlled by a human physical therapist 112 who is interacting with robotic therapist 110. As a result, therapist 112 can remotely guide the patient 12. Robotic therapists 10 and 110 can optionally include cameras and sound systems 200 so that patient 12 and therapist 112 can see and talk to each other.

BRIEF SUMMARY OF THE INVENTION

The invention is generally directed to an internet-based system for rehabilitation of sensory motor skills after brain injury or other injuries. More specifically the invention is a method and a system for remotely and simultaneously providing therapy services to a large number of human patients with sensory motor impairments through a computer network. The patients communicate to a server computer through the computer network from client computers. The server computer downloads individualized information to the client computer that specifies desired therapy and assessment exercises. The therapy and assessment exercises can be performed autonomously without real-time supervision from a therapist. Sensors connected to the client computer measure information about he patient's sensory motor performance. A database on the server computer is updated based on the information from the computerized sensors. The information is analyzed on the server computer and the patients are given individualized, motivating feedback about their motor performance over days. Feedback can be given about how the patient's abilities compare to statistical data form large groups of similar patients who have also used the system.

In the preferred embodiment, the computer network is the Internet, the server computer is a World Wide Web server, and the patient accesses therapy through a standard Web browser. The therapy and assessment exercises are Java applets that are downloaded and executed on the client computer through the Web Browser. The sensor connected to the client computer are mass-manufactured computer input devices, such as a computer mouse, a trackball, or a joystick. Active server pages transmit performance data to the server computer, where it is stored in a database. The patient, or a rehabilitation provider, can access the database through the Web browser to monitor the patient progress over time. Statistical computations can be performed on the server computer to provide patients with an analysis of their progress compared to other similar groups of patients.

The current implementation of the system uses a force feedback joystick to apply therapeutic patterns of force to the arm as the user plays video games, but the software can also be used with a variety of force-feedback and non-force feedback devices. It operates over the Internet using Java, and can track user movement recovery over time and report it to a remote location (e.g. a hospital), as well as back to the user (e.g. at home) for motivational and self-monitoring purposes. The system can also be customized to provide a personalized program of therapeutic exercise.

The current implementation of system makes use of custom software, a commercially available joystick (the Microsoft Sidewinder Force Feedback Pro), a commercially available arm rest (Ergorest), and a custom-designed clip-on handle.

Three principle features of the current system are

1) The methodology as controlled by JAVA software.

The software provides a series of simple movement games for the user (e.g. a stroke patient) to play that are downloaded to the user's computer over the Internet through a Web Browser. It can track user movement recovery over time, storing performance data (e.g. changes in movement speed, accuracy, and smoothness) on a remote server. Thus, a clinician or the user can quantitatively monitor progress in regaining movement ability. Through the use of Java, the software is rapidly modifiable and customizable, and is structured to be platform independent. While Java software is described in the illustrated embodiment and is specifically set forth in the claims, it is to be expressly understood that any software that emulates the performance of Java software to the extent relative to the teachings of the invention is included within the scope of the invention and is within the meaning of the term, "Java", as used in this specification and its claims. The software is also independent of the particular input device, and can be used with a force feedback joystick, a mouse, or other input device. Currently arm rehabilitation is targeted, but the system could also be used with the hand, leg, neck and other body members or muscle groups.

2) Use of a commercial force feedback joystick as a personal movement trainer.

Large, expensive robots for physical rehabilitation of the arm after stroke have been developed by others and by the inventors in other applications. Such systems our bulky, and cost tens of thousands of dollars. The novel insight here was that a commercially available force-feedback gaming joystick, such as that produced by Microsoft, although other companies make similar devices, could be adapted to provide therapy. The joystick costs around $100, and with the software, arm rest, and clip-on handle, is the first viable force-feedback personal movement trainer for individuals after brain injury. However, a variety of other mass-manufactured computer input devices could also be used with the software.

3) The clip-on handle for the joystick.

The clip-on handle makes the system ergonomic for individuals with a brain injury. The handle does not require ability to grasp, and an individual with a one-sided impairment can attach his other hand to it without assistance.

The invention is more fully described in the detailed disclosure of the preferred embodiments. It's primary features are:

1. The software as functionally defined in the disclosure for rehabilitation training;
2. Use of a conventional computer input device in rehabilitation training; and
3. The clip-on handle to the computer input device for those who cannot grasp the computer input device during rehabilitation training.

The present invention is an Internet-based rehabilitation system including, but not limited to, the following:

1. A web-based rehabilitation system and method which monitor rehabilitation status and provide a means to practice rehabilitation activities.
2. A system and method using a library of rehabilitation status tests and therapy activities.
3. A system and method which provide a means to display changes in sensory, motor, and/or cognitive status.
4. A system and method which provide a means to display each user's frequency of use of the status tests and therapy activities.
5. A system and method which provide a means for therapists or caregivers to login and monitor patients ability and usage.
6. A system and method which provide a "to-do-list" of rehabilitation activities to accomplish.
7. A system and method which provide encouraging feedback to the user when the "to-do-list" is accomplished.
8. A system and method which provide a means for therapist or caregivers to customize the "to-do-list".

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Over 730,000 people survive a stroke in the U.S. each year and require rehabilitation to recover lost sensory, motor, and cognitive abilities. Other neurological and orthopedic injuries and diseases impair millions of more people. Currently, there is no Internet-based system available to practice and monitor rehabilitation from these injuries and diseases. There is a loss of strength, coordination, and sensation in the arm and hand due to stroke or traumatic brain injury. With practice, however, they often improve their ability to reach, grasp, and manipulate objects. Significant improvements are possible even several years after brain injury. Physical and occupational therapy are an essential part of recovery, and typically include hands-on manipulations, such as manually assisting in desired arm movements. These manipulations are designed to increase sensory input and stimulate regeneration in the nervous system.

Sensory motor skills improve with increasing levels of therapy. Unfortunately, because of economic pressures on the U.S. health care system, individuals with a brain injury are going home sooner and getting less hands-on therapy Compounding the problem, there is a current lack of technology available for practicing self-therapy at home. To address these needs, several research groups, are developing robotic devices that physically interact with people to stimulate the senses of touch and movement, and to retrain coordinated movement. While preliminary clinical trials are promising for both improved evaluation and therapy, key practical problems with these devices are their cost and size, which may ultimately limit their accessibility and practicality, especially for home use.

The advent of dynamic force feedback technology for the PC, coupled with the networking power of the Internet, could solve these problems. Commercial force feedback joysticks designed primarily for gaming applications can not only sense a person's movement, but can also apply forces during movement. Like existing robotic therapy devices, such devices could be used to stimulate the sense of touch and movement, and could apply therapeutic patterns of forces to the hand and arm as the user attempts to move. Unlike larger robotic devices, however, force feedback joysticks could become truly accessible personal movement trainers because they are already in mass production and can be purchased at low cost. By networking them to rehabilitation centers through the Internet, such devices could provide a means for an individual with a brain injury to access a personalized program of therapeutic exercises, customized by a rehabilitation expert. Also, networking could provide a means for the rehabilitation expert to track the user's sensory motor performance while the user stays at home. Force feedback movement therapy could thus become a viable aspect of tele-rehabilitation services.

With the advent of dynamic force feedback technology coupled with the high-speed communication power of the Internet, a solution to the problem of cost efficient home therapy can be realized. Commercial force feedback joysticks have been available on the market for years and can be purchased for low cost. Although designed primarily to provide special effects in gaming, the joysticks can also be used to apply therapeutic assistive forces as the stroke patient attempts to move. By networking the patient's computer on the Internet, the patient's progress can be recorded and monitored by a therapist while the patient plays from the convenience of his or her own home. The therapist can monitor the progress of the patient without having to be with the patient in person and can further prescribe different activities for the patient by customizing the web site based on the needs of the user. Force feedback movement therapy could thus become a viable aspect of tele-rehabilitation services.

The illustrated embodiment is a home-based rehabilitation system for the training and assessing of arm movement following brain injury. The mechanical parts of the systems are addressed first including the joystick and the mechanical interface required for the patient to interact with the joystick. A detailed description of the software is then discussed, including the software used to control the joystick, the design of the Java based games, and the construction of the web site to monitor patient progress and record data from the games. Finally, an initial two-month evaluation of the system by three stroke patients is described. The illustrated embodiments of the invention are presented for the purpose of illustration and description and are not intended to be exhaustive or to limit the invention to the particular embodiments described. Other embodiments are possible and structural and functional changes may be made without going beyond the present invention's scope.

Consider first the mechanical design aspect of the invention. A Microsoft Sidewinder Force Feedback Pro Joystick 20 was used as the force feedback platform for this project. The joystick 20 required two mechanical modifications in order to make it usable by individuals with a brain injury.

The first modification is a handle redesign. Many individuals with brain injury lose dexterity of the fingers, making grasping difficult. Although the Microsoft handle is ergonomically designed, individuals with brain injury have difficulty in securely grasping it. To address this problem, a new handle was designed that clips on to the preexisting handle. The initial step in creating the new handle design was to survey seven individuals with a brain injury to determine the criteria for a basic shape that would comfortably hold the hand.

Figure 1:
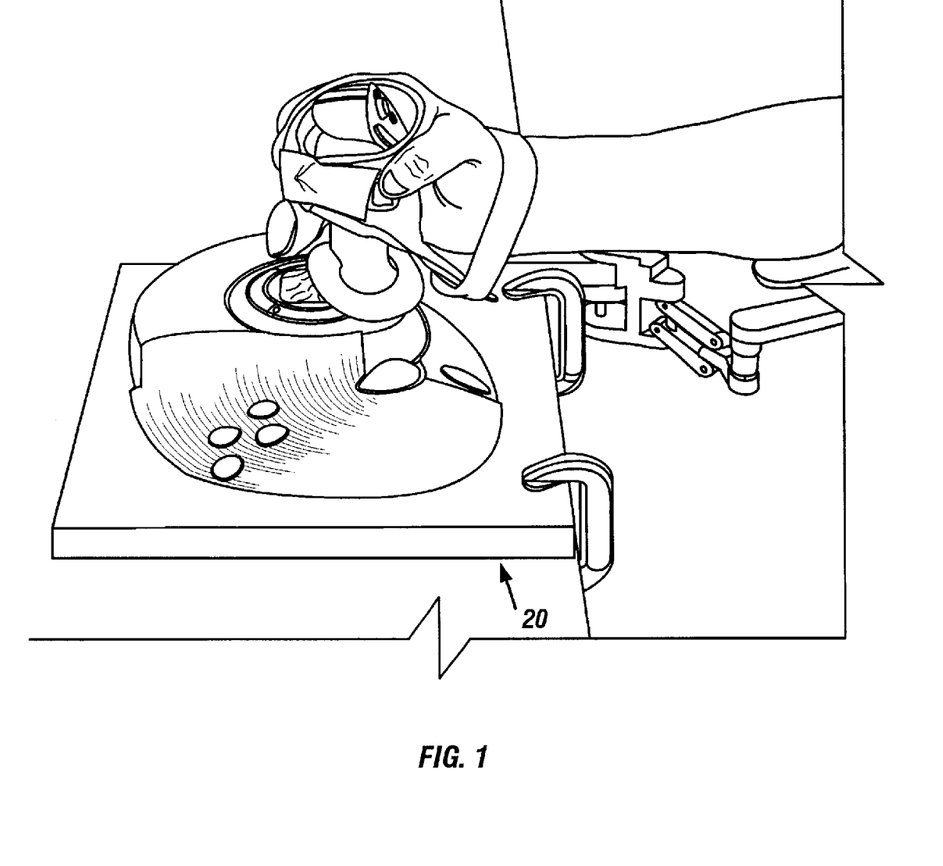
FIG. 1 is a perspective view of a joystick modified according to the invention.

Many prefabricated splints, made out of heat-molded plastics that can be molded when heated, are available for brain-injured people with spastic hands. Four of these splints (conical, U-shaped, ball, anti-spasticity) were tested by seven individuals with brain injury to determine the best splint with regard to comfort and accessibility. The volunteers who were surveyed agreed that a splint with a small conical radius grip, and a splint 24 with a U-shaped grip were the most comfortable and the easiest to hold. It was determined that by slightly modifying the U-shaped splint 24 by bending the top of the U to a more closed shaped, it could be made to mate securely with the joystick handle 26 without using fasteners, and it was thus possible to simply clip it on to the joystick 20. A Velcro strap 22 was added over the back of the hand to help keep the hand engaged to the splint 24. The resulting design holds the hand comfortably and securely, and allows users with one impaired hand to place their impaired hand in the handle using their unimpaired hand as shown in FIG. 1. A similar clip-on splint 24 was designed for the left hand, making the joystick 20 usable by individuals with impairment on either side.

The second modification was in the arm support system. The force feedback joystick 20 was originally designed to provide small special effects to a person's hand and lacks sufficient enough force to accurately control a completely flaccid arm. The Microsoft Sidewinder Force Feedback Pro Joystick can exert a peak force of approximately 1 Kg, which is not enough to move the arm against gravity. In order to overcome this obstacle, an arm rest 32 (Ergorest. Oscar Dellert AB. Finland) was added to the system. The armrest cancels the effects of gravity on the arm, thus resulting in less torque resistance on the joystick motors. This allows the joystick 20 to control the position of the user's hand and arm. The armrest 32, which was designed to support the arm during computer keyboard usage, is comprised of a forearm tray 28 connected to a low-friction, three-joint mechanical linkage 30. It allows the forearm to be positioned and oriented arbitrarily in the horizontal plane and is height adjustable.

Figure 2:
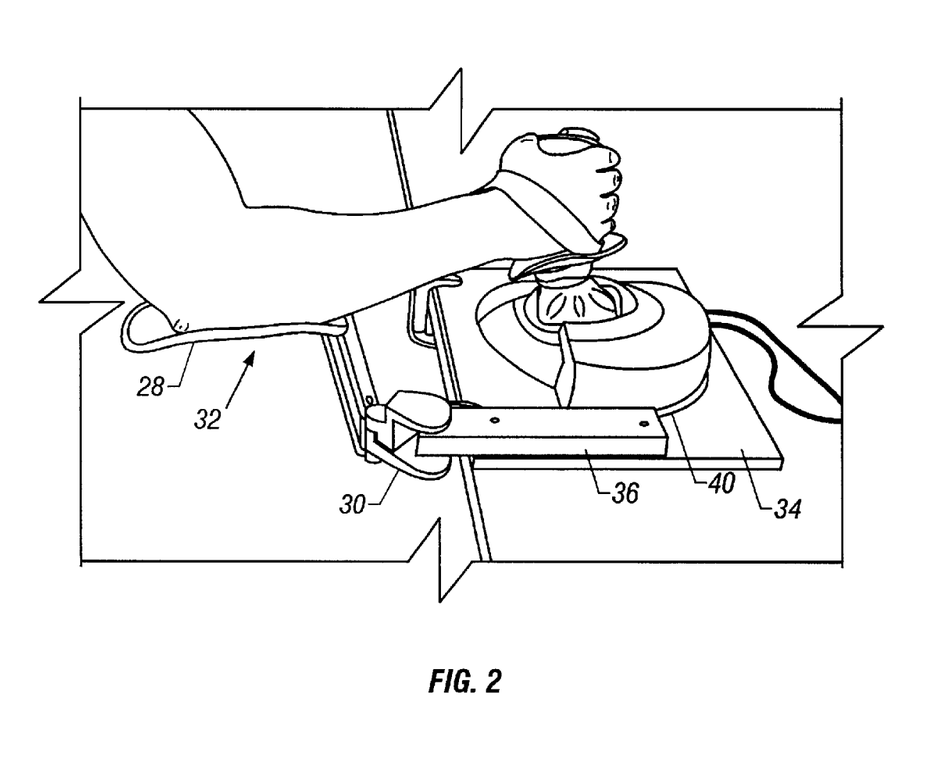
FIG. 2 is a perspective view of a base and an arm combined with the joystick of FIG. 1.

Although the arm splint provides a means for the user to easily grip the joystick, the issue of the joystick sliding around while the user attempts to move it became a problem. To hold the joystick 20 and armrest 32, a wood base 34 with a cutout in the shape of the joystick base was made, and a protruding wood beam 36 was attached to the base 34 for clamping the armrest 32 at the appropriate height. To use the system, the wood base 34 is clamped to a table 38, the joystick 20 is placed inside the cutout 40 to keep it from slipping, and the armrest 32 is adjusted to support the user's arm as shown in FIG. 2. The resulting system allows comfortable movement of the hand in a workspace of approximately six by six centimeters in the horizontal plane.

The Microsoft Sidewinder joystick 20 in FIG. 1 has two degrees of freedom consisting of the X (left/right) direction and the y (up/down) direction. Each degree of freedom is operated by a separate mechanism consisting of a motor, gear train, and a four bar linkage. The high precision DC brush type motors are connected to the gear train, which consists of three gears and yields a gear ratio of 18 to 1. Torque is then transferred from the gear train to the handle via a pivoting four bar linkage. The handle is lightweight to reduce the moment of inertia such that small changes in force are transferred to the user's hand rather than to the handle. The internal components are impregnated with lubricants to reduce friction between the parts and prolong the life of the joystick.

Control of the joystick is accomplished through the use of an onboard microprocessor inside the joystick. The 16-bit microprocessor operates at a speed of 25 MHz and is able to return position and button states with each polling of the joystick. Position sensing of the joystick is accomplished through a small infrared camera mounted underneath the linkage. The camera is able to detect handle motion to within 0.02 degrees. A default set of force effects are stored within the onboard ROM, but the joystick is also built with 2000 bytes of RAM that allow force effects to be downloaded on the joystick and applied. Effects are downloaded through the game port on the back of the computer, which allows for a communication speed between the computer and joystick of 31250 baud.

The next component of the invention is the software design. Two approaches to the software design were considered. The first was to develop a stand-alone program that could be installed on a PC, to control the joystick 20 and to transfer information through a temporary network connection. The second approach was to incorporate force feedback into a web page using a Java applet, and to use the web page to transfer desired information. The first design concept was to create a stand-alone program written in C/C++ that would allow the patient to play therapy games on his or her computer and would write the data to the hard drive in the form of text files.

A stand-alone C/C++ program allows for robust and flexible control of the force feedback effects on the joystick. The data from the game would be picked up on a periodic basis by the therapist.

The alternative to a therapist pick up was to program the C/C++ program to open up an FTP connection to the server computer and transmit the data following a user session. The two major design flaws with the stand alone C/C++ program were that it would be difficult to keep track of which user was using the software at any given time and it would be difficult to make changes in the program quickly since changes would have to be made at each site where the program was loaded.

The second design considered and ultimately implemented was an applet written in Java that would be embedded in a web site. The patient plays therapy games on the applet over the Internet and the data is written to a server computer. The Java applet does not allow for as flexible and robust a control of the force effects as the C/C++ program, but its power lies in its accessibility over the Internet. When a user visits the web site where the Java applet resides, a copy of the Java applet is downloaded onto the user's computer. Thus when changes are required to the applet, they need only be applied at the server computer since the client receives a fresh copy of the applet each time they log into the web site. When the user is done playing the Java based game, the applet automatically transmits the data from the client's computer to the server computer. Due to restrictions in the amount of data that can be posted at one time over a 56K modem, the final design approach was to implement a web site with a Java applet that read data at a low frequency (16.67 Hz) and posted that data to a server combined with a stand-alone Java applet that was run in person with each patient once per month that sampled at a higher frequency (100 Hz). Further, the stand-alone Java sessions allows for observation of the patients while they were playing and allowed for patient feedback as to ways of improving the therapy process.

In order to control the joystick through a Java applet, we used FEELtheWEB software developed by Immersion Corporation. FEELtheWEB is an ActiveX control for Internet Explorer that can apply forces to the joystick 20 and receive function calls through HTML.

Consider now an illustrative embodiment of a therapy game which can be implemented in the invention. A therapy game with force feedback was developed to test the system. The user begins by logging into the system home page using a personal username and password. The user is then taken to a therapy page that downloads a Java applet containing the therapy game onto his or her computer. In the therapy game, the user is asked to move a circular cursor into a square target with the joystick 20 as quickly and accurately as possible. After a delay, if the user has not yet moved into the target, the motors on the joystick 20 activate and assist the hand in moving into the target. This continues for a predetermined number of attempts with the target changing positions to span a 360-degree range of movement directions. For each attempt, the game tracks and records a variety of movement parameters, including the initial and final joystick position, the time when the joystick forces turned on, the total time to complete the trial, and the distance (in pixels) the cursor moved before and after the forces were activated. Upon completion of the game, the data is posted to the server computer.

This implementation of the invention has several advantages:

It is ergonomic for individuals with a brain injury. It does not require ability to grasp, and an individual with a one-sided impairment can attach his or her hand to it without assistance.

It is strong and accurate enough to assist in moving impaired arms to desired locations, provided the arm is supported in an armrest.

It is inexpensive. The joystick and arm support currently retail for around $100. Robotic systems that could achieve similar functionality currently cost tens of thousands of dollars.

It can track user movement recovery over time, storing performance data on a remote server. Its software is rapidly modifiable and customizable.

Its software is structured to be platform independent (currently for non force-feedback pointing devices, and in the future, for force feedback devices).

many users could access the system simultaneously and perform therapy and assessment exercises independently from a therapist.

Software can be employed to display online measures of the user's movement performance as a function of movement practice. This software allows users to self-monitor movement recovery. For example, a person who has just suffered a stroke, and has been released from the hospital, will be able to logon daily from home, practice moving, and determine if his or her arm movement ability has changed. In addition, this capability will ultimately allow remotely located rehabilitation professionals to evaluate users' progress and to make therapy recommendations.

Force feedback is also being incorporated into other games besides the simple game described above. A wide range of freeware Java games are available on the Internet, such as card games, sports simulations, and arcade-style games. A selection of these games is being modified to include force feedback that physically assists in playing the game. Other force-enabled games targeted at training specific deficits in sensory motor performance common after brain injury are also being designed.

The invention allows several key questions for future research to be investigated. For example, to what extent does practicing therapy with the system improve arm movement ability? The system described here provides a powerful new tool for identifying the relationship between movement therapy and recovery. When the system is distributed to a large number of users, and this relationship can be characterized for different types of brain injuries at different times post injury. Users can be informed of their performance with respect to comparable users.

What are the optimal movement therapy techniques? Our initial efforts have focused on using force feedback to assist in movement. However, it is unclear whether such assistance, as opposed to movement practice without assistance or, alternately, with resistance, is the optimal therapy technique. The joystick system provides a means to test what therapy techniques work best for which user groups.

Can the system be applied to rehabilitation of other user populations? With appropriately designed software, people with cerebral palsy, spinal cord injury, Parkinson's disease, orthopedic injuries, and cognitive impairments may also benefit from the Internet-based, force feedback therapy.

Consider now the use of the system of the invention in more generality. The illustrated embodiment, called "Java Therapy" is an Internet-based software system that provides a means to monitor rehabilitation status and practice rehabilitation activities. Patients log on to a website with a username and password. They then choose from a library of rehabilitation status tests, therapy activities, and progress reports. They are also shown a "To Do List" that they can set themselves, or that can be set by their caregiver such as a doctor, therapist, or family member. The "To Do List" shows the patient's actual frequency of use of the status tests and therapy activities, compared to the desired frequency of use. Caregivers can also log on to the site and view progress reports for their patients.

Examples of rehabilitation status tests are:

A speed test that requires the patient to move a cursor into a target, and measures the time to move into the target. The actual x-y points the cursor moves through are also saved every 0.1 second, so that the cursor trajectories can be plotted if desired.

A coordination test that requires the patient to trace a shape such as a figure eight, and measures the tracing error. The cursor trajectory is again saved and can be plotted to see the shape of the figure eight the patient traced.

A finger speed test that requires the patient to click the mouse button as many times as possible in ten seconds, and measures the number of clicks.

A strength test that requires the patient to hold his or her hand as still as possible as a force-feedback joystick tries to move it, and measures the total distance moved.

A functional evaluation test in which the patient or caregiver scores the patient's ability to achieve specific movements, such as touching the chin.

A timed evaluation test, in which the patient uses the Java Therapy software to time how long it takes to perform a specific task, such as tying a knot in a rope.

Examples of therapy activities are:

A Breakout therapy activity, in which the patient moves his or her hand to control a paddle on the screen and rebound a moving ball into a bank of targets so that the targets are destroyed. The system keeps track of the number of targets destroyed each time the game is played. When a force feedback joystick is used with the system, the Java Therapy system can physically assist or resist in hand movement as the patient plays the game.

A Blackjack therapy activity, in which the patient clicks buttons in order to deal, hit, and hold cards.

Any rehabilitation status test performed as a therapeutic activity.

Range of motion or strengthening exercises that are described on the computer screen.

Examples of progress reports are:

A progress report that informs the patient of his or her scores on the status tests or therapy activities. The progress report also shows the target score for the patient, and compares their current performance to their average past performance and their last performance to indicate if his or her rehabilitation status is changing.

A progress report that displays the patient's scores on the status tests or therapy activities as a function of time or as a function of the number of tests or activities performed. The progress report also shows the target score for the patient, which can be set by the patient or the patient's caregiver.

The "To Do List". when the actual frequency for an activity exceeds the desired frequency, the system places encouraging feedback on the "to-do list", such as writing "Good Job!" next to the activity.

The system can be used with a variety of input devices, including a standard computer mouse, a wireless, gyroscopic computer mouse, a standard keyboard, and a force feedback device such as a force feedback joystick or mouse. If a force feedback device is used, the device can physically resist or assist in movement of the patient, such as in the strength test or in the Breakout therapy activity.

Figure 3:
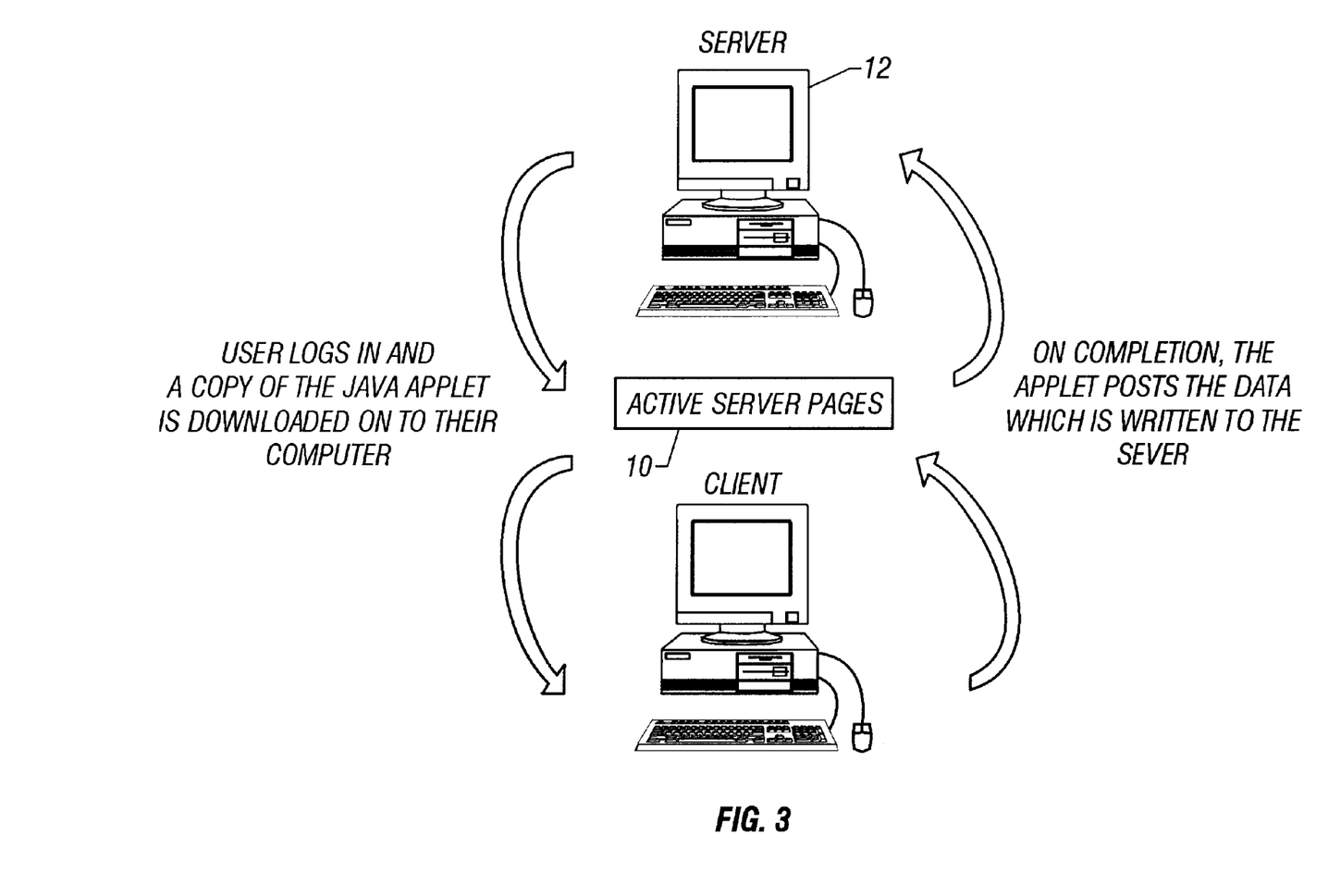
FIG. 3 is a simplified block diagram illustrating the concept used in the JAVA Therapy version of the invention as practiced on the Internet.
Figure 4:
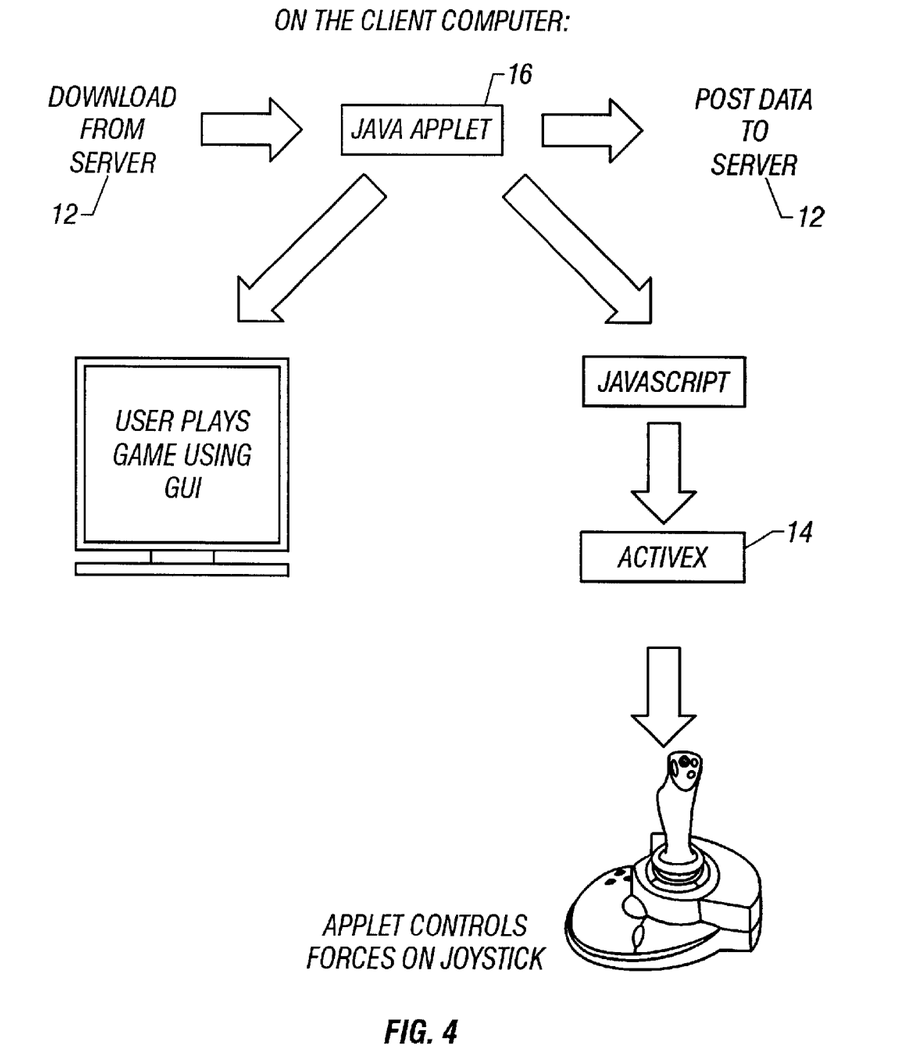
FIG. 4 is a simplified block diagram illustrating the client side processing used in the system of FIG. 4.

The system is implemented as shown diagrammatically in FIGS. 3 and 4 using a combination of hypertext markup language (HTML), active server pages 10 (ASP's), Active X controllers 14, Java applets 16, and Perl code, and runs on an Windows NT Web Server 12 with Microsoft Access database as well as a text-file based data base. Use of Java applets 16 allows client side processing as shown in FIG. 4. The system currently works best with Windows Explorer on a PC, but is compatible with Netscape Navigator and Macintosh. The software could easily be modified to run without requiring a continuous connection to the Internet. In this case, it would transmit and receive information from the centralized database at night or periodically through the day.

The design of the web site for the patients represented the core work with the web based Java project. The web site allows for the logging of individual patients as they access the web site as depicted in FIG. 3 as well as all the functionality required to control the joystick 20 and run the Java therapy games as depicted in FIG. 4. Consider now the various elements that went into designing the web site.

An ActiveX controller 14 is a marketing name for the set of technologies and services all based on the Component Object Model (COM). Any device that supports this COM service can communicate with another device that also supports the COM technology. In our case, the ActiveX controller 14 is software that can implement forces on the joystick 20 and take commands from over the Internet. The ActiveX controller 14 used for this project is the FEELtheWEB software developed by Immersion Corporation. The ActiveX controller 14 is installed on the user's computer and control functionality for the ActiveX controller 14 is embedded directly on the HTML document where forces are required. By calling scripting functions supported by the embedded ActiveX controller, the web site can command the forces on the joystick 20. Calling the ActiveX's Make <Force Effect> function first creates forces.

The <Force Effect> values available to the ActiveX controller 14 include spring forces, constant forces, damping forces, ramp forces, sinusoidal forces, and barrier forces. Once the forces are created, calling the ActiveX's Start <Force Effect> function starts them. Further, certain parameters of the forces can be dynamically changed. In the case of the spring force, for example, the stiffness and center can be changed. By manipulating the force parameters, the desired control for the joystick was obtained.

HTML documents are one of the most universally known types of Internet documents. An Active Server Page (ASP) document is identical to an HTML document with one exception. While an HTML document contains only client side scripting, an ASP document can contain server side scripting as well as client side scripting. It is important to understand the distinction between client side and server side scripting. While client side scripting can only affect things on the user's computer, server side scripting can not only affect how a user sees the web page on his or her computer, but it can also manipulate files and objects on the server computer. Since a Java applet is a client side entity, the ASP pages are necessary for writing the applet data onto the server. When the Java applet is ready to transmit its data, the data is encoded and posted to an ASP page, which in turn takes the data and writes it to a file on the computer. The other benefit of using ASP pages is that ASP variables are constant throughout a user's session. For example, a user begins their web session at a login page. The user logs in using his/her own username, which is written to the ASP variable, Session ("Username"). As the user navigates through the web site, the Session ("Username") variable remains constant and is used to distinguish one user's data from another user's data. Although not implemented in preliminary trials, ASP variables can also be used to track other data such as user skill level and user playing time. These values can be used to customize each user's session by writing user data into the tag of the Java applet. For example, a user that requires a higher magnitude of assistive forces might have a higher user level as designated by the user's login profile. The user level can also be saved in a Session variable and written to the Java applet tag where the Java applet can read in this number and increase the magnitude of forces used during the game based on this user level.

JavaScript is the scripting language that allows for control of the ActiveX control which implements the forces on the joystick. The JavaScript is used to call ActiveX functions that create the force effects. For this case, the JavaScript creates a spring force, which is then downloaded into the joystick. The JavaScript functions can be called from the Java applet using the Netscape Live Connect package and by using the MAYSCRIPT tag in the applet tag. In this way, the Java applet can control what forces are applied on the joystick.

Figure 5:
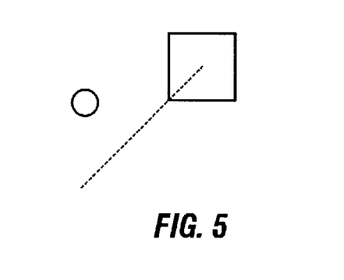
FIG. 5 is a diagram depicting the display of the circle therapy game.
Figure 6A:
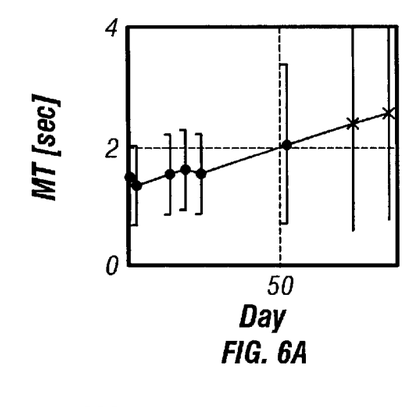
FIG. 6 are graphs of four subjects showing in the top row movement time to complete a trial, the middle row distance moved after force activation, and in the bottom row total cumulative practice time. Standard deviations re shown in vertical bars in each graph.
Figure 6B:
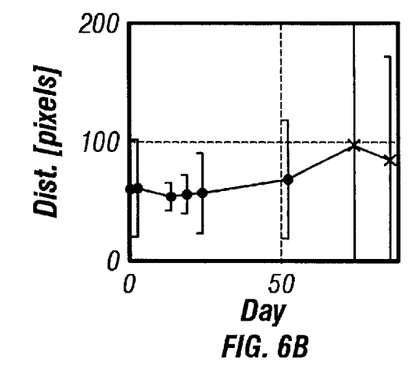
Figure 6C:
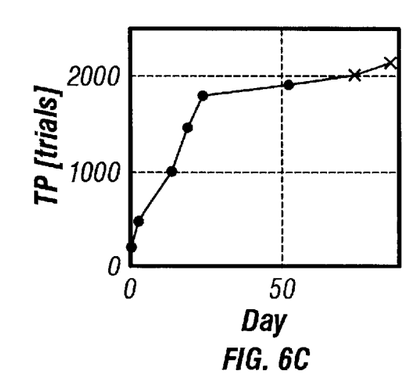
Figure 6D:
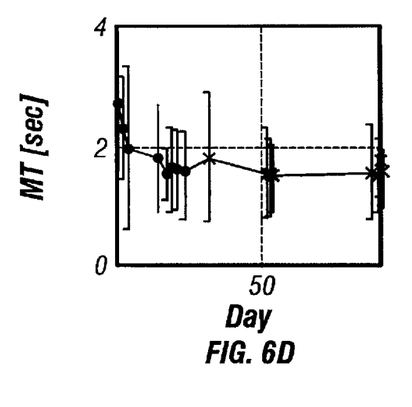
Figure 6E:
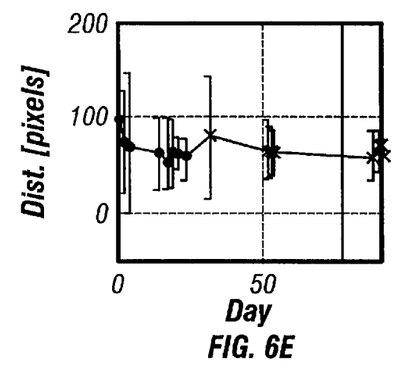
Figure 6F:
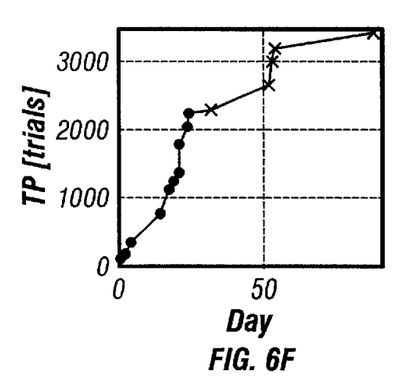
Figure 6G:
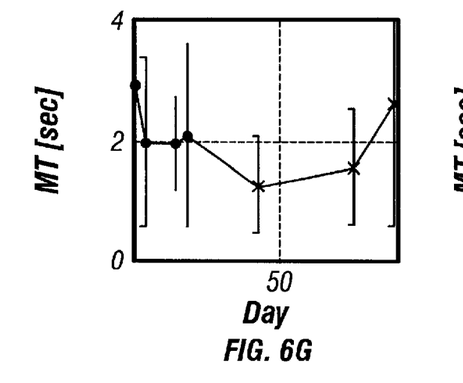
Figure 6H:
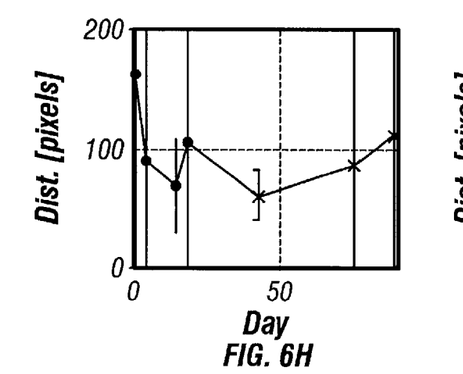
Figure 6I:
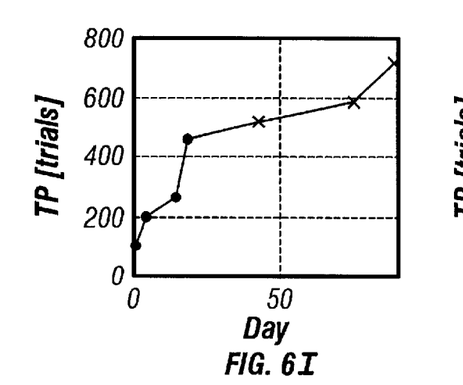
Figure 6J:
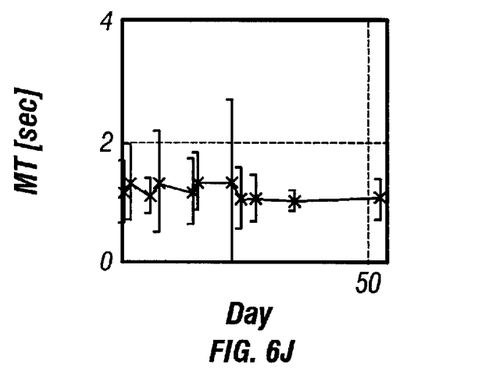
Figure 6K:
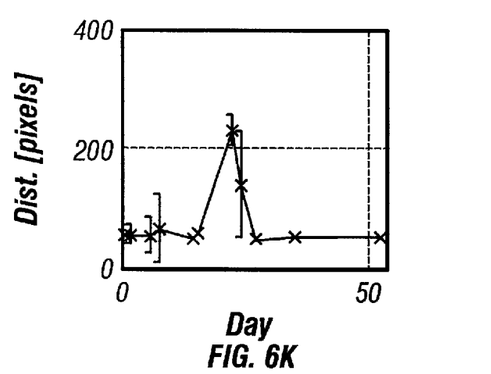
Figure 6L:
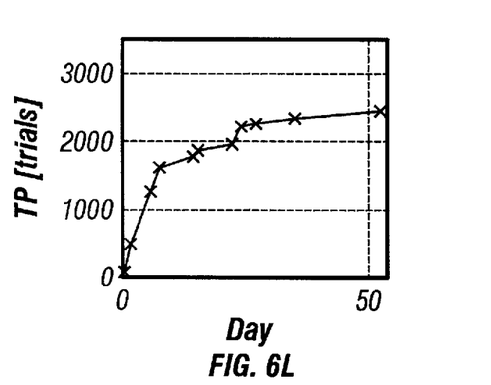

The preliminary Java applet designed for use, Circle Therapy (Appendix A filed herewith and available in the U.S. patent file history of this application), was made to test the patient's speed and coordination. In the game described above, the patient controls a circular cursor with the mouse as depicted in FIG. 5 and his/her goal is to move the circular cursor inside the square target as accurately and quickly as possible. One trial consists of entering the target and remaining there for a duration of 0.5 seconds. At this point, the target disappears and reappears at one of eight random locations. This continues for a pre-determined amount of trials. If the user is unable to move the cursor within the target within a certain amount of time, the applet turns on the motors in the joystick and provides assistive forces to move the user into the target. If the user is still unable to move the cursor into the target, the trial automatically ends after six seconds. After the trial, the forces then shut off to allow the user an opportunity to move into the next target. As the user plays the game, the applet records the time and cursor position internally and posts all the information upon the conclusion of all trials.

Like C and C++, Java is written utilizing OOP (Object Oriented Programming). By using OOP, different classes can be written that encompass all the different objects in the game. This allows functions for each class to be written independently of the other classes that allow for manipulation of objects create from that class. For example, a class called "Space Ship" could be written that allows for the creation of multiple "Space Ship" objects. Some different functions written for the "Space Ship" class might be "Thrust" or "Brake" or instance. These functions can be called for each individual "Space Ship" object to allow for the movement of a particular "Space Ship" object.

For the purposes of this Java applet, three different Java classes were created. The first Java class is the Circle Therapy class which encompasses the core of the applet. The "main" function resides within this class as well as all threading. A thread automatically updates the applet at a certain time period and allows the applet to "run" at a certain frequency. In this case, the applet updates itself at a frequency of 100 Hz and updates the Game Area class at this frequency. The second class written for the Java applet is the Game Area class. This is the most important class of the applet as it handles all functionality of the game. The Game Area class draws the main game area, the circle cursor, and the target cursor. As the applet runs, the Game Area class is also responsible for updating the locations of all the objects, checking if forces need to be applied, and logging all data as a result of the user's movements. The final class is the Helper Force class, which is responsible for communicating with the JavaScript on the web page that the applet is embedded on. A Helper Force object is created in the Game Area class and functions from the Helper Force object are called when forces are needed. For example, when the unassisted time duration has expired in the game and the user is not in the target yet, the Game Area calls the "doforces" function in the Helper Force class, which commands the ActiveX to turn on the spring forces.

Two different types of control were utilized for moving the user towards the desired target by means of an assistive force. The first type of control is a proportional control utilizing only a spring force. A spring force is created and initially its stiffness is set to zero. The center of the spring is dynamically changed during each trial to correspond to the center of the desired target location. Once the one-second-time period has been exceeded, the stiffness is reset to maximum and the spring forces help drag the joystick into the target since the force is not proportional to the distance the user is from the target center. Upon completion of the trial, the spring stiffness is reset back to zero. It was found that for users with heavy hands and thus high moments of inertia on the handle, the spring forces were not always adequate enough to move the user into the target. A ramp force was then added to augment the spring force.

This ramp force pushes in the direction of the target center and incrementally increases until the user is within the target. A ramp force was used rather than a constant force in order to prevent instability in the case of overshooting the target. The web based Java therapy used the combination spring and ramp forces, while a comparison of spring alone versus spring plus ramp forces was done for the stand-alone version.

The therapy system was tested by four subjects with hemi paresis as a result of stroke. The first three subjects were volunteers from a local outpatient rehabilitation center while the fourth used the system from home. All the subjects were given dial up modem access at UCI in order to access the web site. Each subject was also given a username and password to log into the web site so that their data would be distinguishable from each other. Subjects 1,2,3, and 4 were aged 53, 32, 52, and 63, and were 5, 2, 4, and 1 years post-stroke respectively. They had different levels of arm impairment classified as mild, moderate, severe, and mild according to a clinical scale. Each subject was asked to participate in the web-based therapy for a period of two months in addition to a stand-alone therapy session each month. The first three patients began their therapy at the end of September 1999 and data was recorded up until December 1999. The fourth patient began his therapy in the middle of October 1999 and data was recorded up until December 1999.

The web based Java game used a combination of spring and ramp forces to assist the user in moving into the target. Up until the middle of October, the forces were designed to activate after a time period of two seconds. This was done in order to give the patient the opportunity to move into the target themselves since it was determined that a normal person could move from target to target in one second. After the middle of October, the forces were activated after a time period of one second in order to match the time that the stand-alone version forces were activated.

This was done such that the testing conditions of the therapy were the same for the web version versus the stand-alone version. In the case of the web-based therapy, the distance from the target at the time the forces activated and the time taken to complete each trial were recorded. This data was plotted over a two-month period of time as well as the patient's usage over the two-month period (Appendix C filed herewith and available in the U.S. patent file history of this application).

Due to restrictions in the amount of data that can be posted on the web site, it was necessary to create a stand-alone version of the Java therapy. The difference between the standalone and the web based versions is that although both versions ran at a frequency of 100 Hz, the web based version samples data at only 16.67 Hz while the stand-alone version samples data at the running speed of 100 Hz. The stand-alone version lasts for a duration of 96 trials with half the trials using assistive forces and the other half without any kind of assistive forces. The data collected from the stand-alone version differed from the web-based version in that the stand-alone version recorded mouse coordinates as a function of time. The stand-alone version was also designed to use either spring only assistive forces or spring plus ramp assistive forces. The standalone was used to get more accurate data from the patients, compare performance between spring and spring plus ramp forces, and ascertain improvements in the patient's movement by comparing forces off movement over a two month time period.

The stand-alone version of the Java therapy was conducted in person with the first session run one week after the beginning of the web based therapy. This was done to give the user an ample opportunity to become familiar with the web site and with the therapy that would be conducted. The data from the stand-alone sessions was analyzed (Appendix D filed herewith and available in the U.S. Patent file history of this application) and plots were made of the distance from the target as a function of time. The first plot shows the case when the forces are off and a comparison of the patient's movement ability over the two-month time period can be determined. The second set of three plots show the standard deviation of the patient over the two-month time period and are used to show improvements in consistency. The last set of plots shows a comparison of the patient's movement ability with and without the forces active.

These plots help determine if the forces actually assist the patient in getting to the target at a higher rate.

From the web-based data as shown in FIG. 6, it shows that subject I remained relatively consistent in all areas with the exception of the movement time towards the end of the study time.

Figure 7:
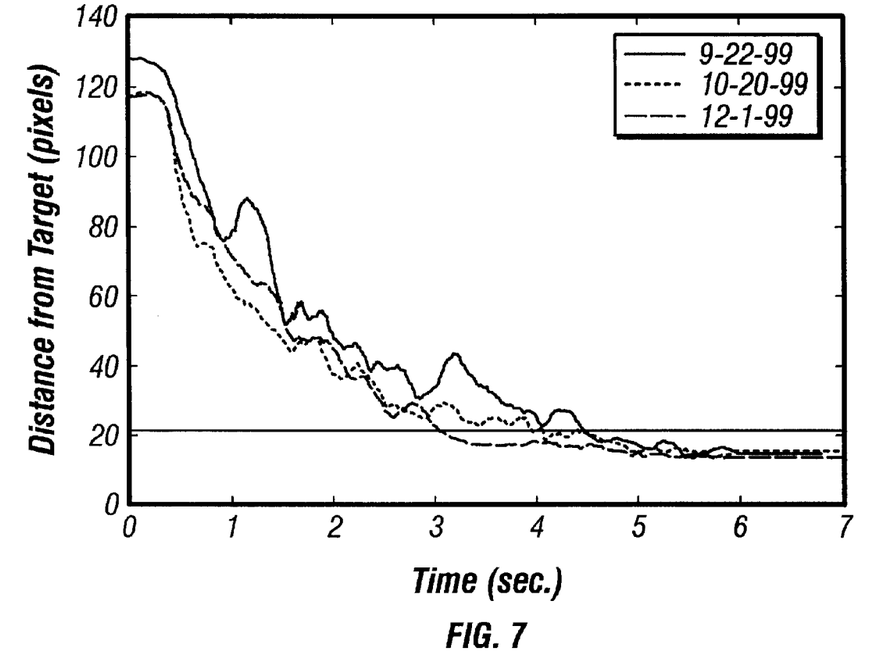
FIG. 7 is a graph of subject #3 for stand alone data.

Subject 1, the mild case, also shows a worsening trend in moving starting at 52 days. Subject 2, the moderate case, shows improvement in both moving time and distance for the first thirty days and remains consistent at the same level for all times beyond. Subject 3, the most extreme case, shows gradual improvement up until 42 days into the study and then shows a worsening trend towards the latter part of the experimental time. Subject 4, the last mild case, remains consistent throughout the experimental time period with the exception of a couple bad data points towards the middle of the experiment. The usage of all the patients as shown in FIG. 7 was plotted and it shows that the therapy usage begins to curtail towards the end of the experiment.

Figure 8:
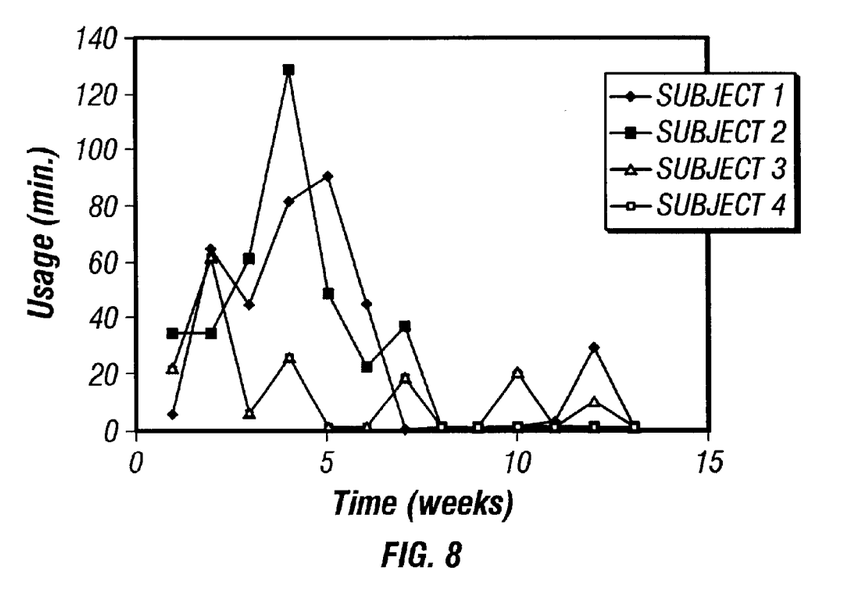
FIG. 8 is a graph showing patient usage of the web based system over a period of weeks.
Figure 9:
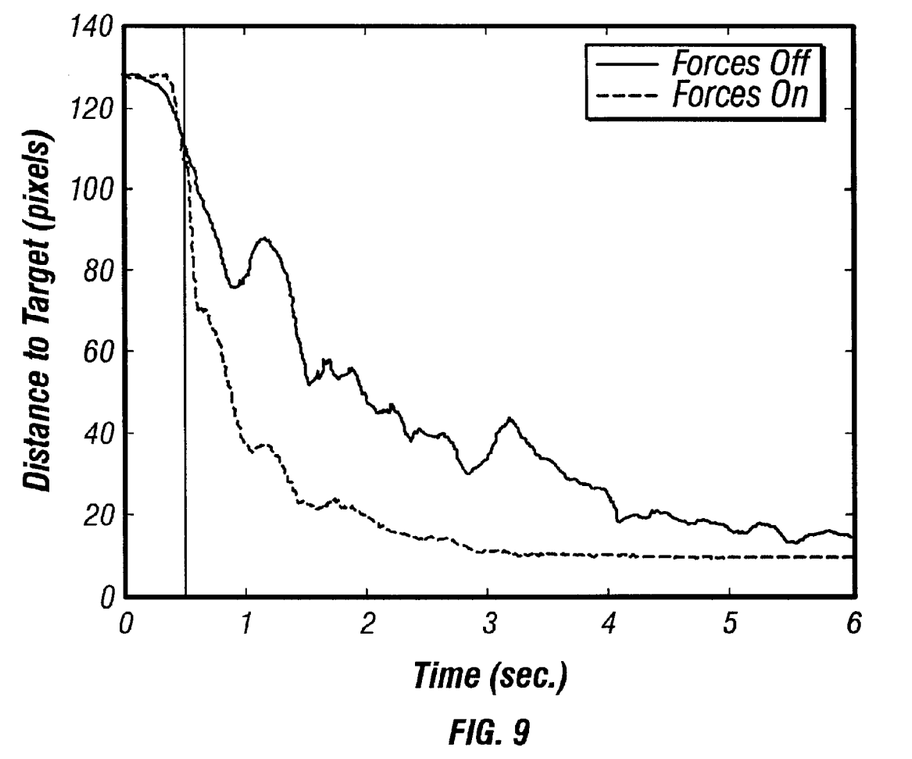
FIG. 9 is a graph illustrating the effect of assistive forces for subject #3.

From the stand-alone therapy data, only in the case of subject 3 is there any appreciable change in movement ability as shown in FIG. 8. In all other cases, the patients remain consistent are able to move into the target in the same amount of time over the entire two month period of time. For the comparison of forces versus no forces, the data shows that with forces active, subjects 2 and 3 as shown in FIG. 9 were able to get into the target faster. For the cases of subject 1 and 4, the forces had negligible effect and the patients were able to get into the target just as quickly with or without forces.

The worsening of Subject 1's condition can be attributed the forces actually becoming disruptive when forces were activated earlier expected. The web results show that for the severe and moderate case patients, the therapy seems to be beneficial as their performance improves in beginning. It is still unknown why the severe patient begins to worsen towards the hind part of the experiment and further experiments may be necessary to completely validate the therapy's ability to improve patient performance. The results from the patient' usage also show that the patient' interest in participating in the therapy curtails at around six weeks. This is the point where the patients are becoming bored of participating in the therapy due to the monotony of the therapy game. This trend can also be seen as the total cumulative practice times gradually levels off towards the end of the experimental session time. It can be concluded that in order to successfully implement a therapy of this kind on the Internet, it will be necessary to implement a wide variety of other therapy games in order to stimulate the interest of the user. Examples would include everyday games such as blackjack, solitaire, fishing, etc: Any game that can be setup to record data and can implements forces on the joystick would be useful for this case.

From the stand-alone therapy data, it can be concluded that the assistive forces were only really helpful for subject 3, the patient rated as severe. In all other cases, the patients were able to move into the target before the forces could activate to provide assistance at the one-second-time duration. Consequently, only the third subject showed any kind of improvement over the two month time period while the rest of the patients remained consistent over the testing period. This shows that although assistive forces are successful in improving movement ability in a severe patient, they do not stimulate improved movement in a patient that as not had a severe stroke. Therefore, it may be necessary to add additional therapy games that use resistive rather than assistive forces to challenge a patient that has not had a severe stroke. From the ramp versus no ramp forces, it can be concluded that the forces are beneficial in assisting the patients for the cases where the patient has had a moderate or severe stroke. For the other two subjects, the forces were irrelevant since the patients were able to navigate to the target faster than the forces could be applied.

From the collected data, it appears that the therapy is beneficial to persons with a moderate or severe disability. In order to make the therapy a viable solution for a wider range of people with varying levels of stroke and brain injury, several improvements to the illustrated embodiment can be made and are expressly included within the scope of the invention. The following additions would improve the system:

The addition of a greater variety of games supporting force feedback to stimulate more interest in playing on the web site.

The addition of resistive as well as assistive forces to provide force feedback therapy to persons with mild stroke or brain injury.

An interactive therapist database that would allow a therapist to customize the game programs depending on the level of the user.

The results from this study have already been implemented in a new version of the webbased therapy. This new version uses four different therapy games for tracking patient performance. The first is a speed game, which is essentially the same game as the first version of the web page with the exception that there are no forces and the game measures the un-assisted user movement. The second game measures the user's coordination as the user traces circles using the joystick. Again, this game uses no forces and measures the user's un-assisted coordination. The third game is the strength game, which uses resistive forces to try and knock the user's cursor out of a square and measures the user's arm strength. The final game is a finger clicking game which measures the user's finger coordination as the user attempts to click the mouse or joystick button as many times as possible in an allotted amount of time.

The new version of the web site also utilizes fun activity games meant to stimulate the user's interest in the web site. These games record only the time the user spends playing them but are still an important part of the therapy process as the user is benefiting with the more time he or she spends on the site. These games include a blackjack game, an Othello game, and a breakout game. Currently only the breakout game supports force feedback technology as the game provides assistive or resistive forces to help or hinder the user based on the user type.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A method for remotely providing therapy services to a human patient having impaired function of a limb through a computer network, said patient communicating to a server computer through said computer network from a client computer, said method comprising:

coupling a conventional mass-produced computer input device to said client computer;

modifying said conventional mass-produced computer input device to provide a secure connection between said conventional mass-produced computer input device and said impaired limb of said patient whereby said patient may effectively engage said conventional mass-produced computer input device;

providing a rest for said limb for supporting said limb of said patient; and providing interactive video feedback to said patient in response to a predetermined desired therapeutic exercise.

2. The method of claim 1 where providing said conventional mass-produced computer input device comprises providing a force feedback joystick.

3. The method of claim 1 where providing said conventional mass-produced computer input device comprises providing a mass-produced computer mouse.

4. The method of claim 1 where providing said conventional mass-produced computer input device comprises providing a mass-produced trackball.

5. The method of claim 1 further comprising monitoring rehabilitation status of said patient using client sided computer applets downloaded between said server computer and said client computer.

6. The method of claim 1 further comprising providing a library of rehabilitation status tests using client sided computer applets downloaded between said server computer and said client computer.

7. The method of claim 1 further comprising providing a library of therapy activities using client sided computer applets downloaded between said server computer and said client computer.

8. The method of claim 1 further comprising displaying changes in sensory, motor, and/or cognitive status of said patient using client sided computer applets downloaded between said server computer and said client computer.

9. The method of claim 6 further comprising displaying said patient's frequency of use of said status tests using JAVA based software communication.

10. The method of claim 7 further comprising displaying said patient's frequency of use of said therapy activities using client sided computer applets downloaded between said server computer and said client computer.

11. The method of claim 1 further comprising monitoring through said computer network a patient' performance and frequency of exercise using client sided computer applets downloaded between said server computer and said client computer.

12. The method of claim 1 further comprising providing a "to-do-list" of rehabilitation activities for said patient to accomplish using client sided computer applets downloaded between said server computer and said client computer.

13. The method of claim 12 further comprising providing encouraging feedback to said patient when said "to-do-list" is accomplished using client sided computer applets downloaded between said server computer and said client computer.

14. The method of claim 12 further comprising customizing said "to-do-list" for said patient through said computer network using client sided computer applets downloaded between said server computer and said client computer.

15. An apparatus for remotely providing therapy services to a human patient having impaired function of a limb through a computer network, said patient communicating to a server computer through said computer network from a client computer, said apparatus comprising:
   a conventional mass produced computer input device coupled to said client computer;
   a splint coupled between said conventional mass produced computer input device and said limb of said patient whereby said patient may effectively engage said conventional mass produced computer input device;
   a rest for elevating and maintaining a predetermined position of said limb of said patient; and
   means for providing interactive video feedback to said patient in response to a predetermined desired therapeutic exercise.

16. The apparatus of claim 15 where said mass produced computer input device is a force feedback joystick, where said rest is arranged and configure to cancel the effects of gravity on said limb, thus resulting in less torque resistance applied to said force feedback joystick, and where said means for providing interactive video feedback to said patient also provides an assistive force to said limb through said force feedback joystick.

17. The apparatus of claim 16 where said force feedback joystick is a mass produced, unmodified force feedback joystick.

18. The apparatus of claim 15 further comprising means for monitoring rehabilitation status of said patient using client sided computer applets downloaded between said server computer and said client computer.

19. The apparatus of claim 15 further comprising means for providing a library of rehabilitation status tests and therapy activities using JAVA based software communication using client sided computer applets downloaded between said server computer and said client computer.

20. The apparatus of claim 15 further comprising means for displaying changes in sensory, motor, and/or cognitive status of said patient using client sided computer applets downloaded between said server computer and said client computer.

21. The apparatus of claim 15 further comprising means for displaying said patient's frequency of use of said status tests and therapy activities using client sided computer applets downloaded between said server computer and said client computer.

22. The apparatus of claim 15 further comprising means for monitoring through said computer network a patient' performance and frequency of exercise using client sided computer applets downloaded between said server computer and said client computer.

23. The apparatus of claim 15 further comprising means for providing a "to-do-list" of rehabilitation activities for said patient to accomplish using client sided computer applets downloaded between said server computer and said client computer.

24. The apparatus of claim 23 further comprising means for providing encouraging feedback to said patient when said "to-do-list" is accomplished using client sided computer applets downloaded between said server computer and said client computer.

25. The apparatus of claim 23 further comprising means for customizing said "to-do-list" for said patient through said computer network using client sided computer applets downloaded between said server computer and said client computer.

26. A method for remotely providing individualized therapy services to a multiplicity of human of patients with sensory motor impairments through a computer network, said patients communicating to a server computer through said computer network from a corresponding multiplicity of client computers, said method comprising:
   downloading individualized information from said server computer to said client computer in which said individualized information specifies a therapy and assessment exercise for said patient to perform;
   providing said therapy and assessment exercise that can be performed autonomously without real-time supervision of a therapist;
   measuring said patient's sensory motor performance with sensors or input devices coupled to said client computer;

updating a database on said server computer based on information from said sensors or input devices;

analyzing said information on said server computer; and downloading said analyzed information to said client computer to provide individualized, quantitative feedback about said patient's sensory motor performance over time.

27. The method of claim 26 further comprising comparing said patient's sensory motor performance to an average performance of similar patients, and displaying said comparison to said patient.

28. The method of claim 26 further comprising providing access to said server computer from one of said client computers to a rehabilitation service provider, examining said patient's sensory motor performance for an individual patient, and providing to said server computer a modified therapy program for said individual patient.

29. The method of claim 26 further comprising providing mass-manufactured computer input or gaming devices as said sensors or input devices.

30. The method of claim 26 further comprising providing a World Wide Web server as said server computer, a Web browser for providing access from said client computer to said server computer, and an Internet communication between said server computer and client computer.

31. The method of claim 26 where downloading individualized information from said server computer to said client computer comprises downloading client-side computer applets from said server computer and executing said client-side computer applets on said client computer.

32. An apparatus for remotely providing individualized therapy services to a multiplicity of human of patients with sensory motor impairments through a computer network, said patients communicating to a server computer through said computer network from a corresponding multiplicity of client computers, said apparatus comprising:

means for downloading individualized information from said server computer to said client computer in which said individualized information specifies a therapy and assessment exercise for said patient to perform;

means for providing said therapy and assessment exercise that can be performed autonomously without real-time supervision of a therapist;

means for measuring said patient's sensory motor performance with sensors or input devices coupled to said client computer;

means for updating a database on said server computer based on information from said sensors or input devices;

means for analyzing said information on said server computer; and means for downloading said analyzed information to said client computer to provide individualized, quantitative feedback about said patient's sensory motor performance over time.

33. The apparatus of claim 32 further comprising means for comparing said patient's sensory motor performance to an average performance of similar patients, and means for displaying said comparison to said patient.

34. The apparatus of claim 32 further comprising means for providing access to said server computer from one of said client computers to a rehabilitation service provider, means for examining said patient's sensory motor performance for an individual patient, and means for providing to said server computer a modified therapy program for said individual patient.

35. The apparatus of claim 32 further comprising mass-manufactured computer input or gaming devices as said sensors or input devices.

36. The apparatus of claim 32 where said server computer comprises a World Wide Web server, said client computer includes a Web browser for providing access to said server computer, and where said computer network is an Internet communication between said server computer and client computer.

37. The apparatus of claim 32 where said means for downloading individualized information from said server computer to said client computer comprises means for downloading client-side computer applets from said server computer and means for executing said client-side computer applets on said client computer.

38. A method for remotely providing individualized therapy services to a multiplicity of human of patients with sensory motor impairments through a computer network, said patients communicating to a server computer through said computer network from a corresponding multiplicity of client computers, said method comprising:

downloading individualized information as client-sided computer applets from said server computer and from said server computer to said client computer in which said individualized information specifies a therapy and assessment exercise for said patient to perform;

executing said client-side computer applets on said client computer;

providing said therapy and assessment exercise that can be performed autonomously without real-time supervision of a therapist;

measuring said patient's sensory motor performance with sensors or input devices coupled to said client computer;

updating a database on said server computer based on information from said sensors or input devices;

analyzing said information on said server computer; and downloading said analyzed information to said client computer to provide individualized, quantitative feedback about said patient's sensory motor performance over time.

* * * * *